United States Patent [19]

Giersberg et al.

[11] Patent Number: 4,983,750
[45] Date of Patent: Jan. 8, 1991

[54] PHOSPHOBETAINES, METHODS FOR THEIR SYNTHESIS AND THEIR USE ESPECIALLY FOR INDUSTRIAL PURPOSES

[75] Inventors: Joachim Giersberg, Recklinghausen; Hans-Joachim Kollmeier, Essen, both of Fed. Rep. of Germany

[73] Assignee: Th. Goldschmidt AG, Essen, Fed. Rep. of Germany

[21] Appl. No.: 371,497

[22] Filed: Jun. 26, 1989

[30] Foreign Application Priority Data

Aug. 6, 1988 [DE] Fed. Rep. of Germany ....... 3826805

[51] Int. Cl.$^5$ .............................. C07F 9/02; C07F 9/10
[52] U.S. Cl. .................................... 558/134; 558/135; 558/170; 260/403
[58] Field of Search ....................... 558/134, 135, 170; 260/403

[56] References Cited

U.S. PATENT DOCUMENTS

| | | | |
|---|---|---|---|
| 2,635,112 | 4/1953 | Fields | 558/135 |
| 4,215,064 | 7/1980 | Lindemann et al. | 260/403 |
| 4,231,903 | 11/1980 | Lindemann et al. | 252/545 |
| 4,283,542 | 8/1981 | O'Lenick, Jr. et al. | 548/112 |

FOREIGN PATENT DOCUMENTS 2260326 6/1973 Fed. Rep. of Germany .

Primary Examiner—Cecilia Shen
Attorney, Agent, or Firm—Toren, McGeady & Associates

[57] ABSTRACT

Phosphobetaines of the general formula

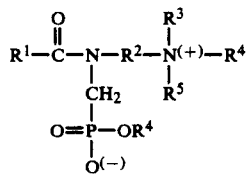

are disclosed in which $R^1$ is an alkyl group with 1 to 20 carbon atoms, optionally substituted with OH groups, or the

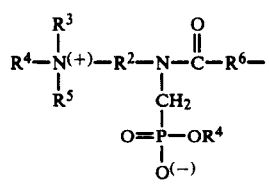

group, in which $R^6$ is a divalent alkylene group with 1 to 10 carbon atoms, optionally substituted with OH group, $R^2$ is a divalent hydrocarbon group with 2 to 10 carbon atoms, the chain of which may be interrupted by one or more nitrogen atoms, $R^1$, $R^5$ are the same or different and represent alkyl or benzyl groups and $R^4$ is an alkyl group with 1 to 4 carbon atoms.

Also disclosed is the synthesis of these compounds and their use as surface active substances, preferably for the treatment of polar surfaces in the industrial area.

3 Claims, No Drawings

PHOSPHOBETAINES, METHODS FOR THEIR SYNTHESIS AND THEIR USE ESPECIALLY FOR INDUSTRIAL PURPOSES

FIELD OF THE INVENTION

The invention is directed to novel phosphobetaines and their synthesis. The invention furthermore is directed to the use of these novel phosphobetaines as surface active substances, especially in the industrial area.

More particularly, the invention relates to novel phosphobetaines with increased resistance to hydrolysis and a novel method, which permits the synthesis of salt-free and especially alkali salt-free phosphobetaines.

BACKGROUND INFORMATION AND PRIOR ART

Phosphobetaines are known from the art. They have excellent foaming properties, are wetting agents and detergents, have antistatic activity and can be used as emulsifiers in numerous technical areas. They are tolerated excellently by the skin, irritate the conjunctiva of the eye only slightly and have a low oral toxicity. They are therefore especially suitable for cosmetic preparations for the care of the skin and the hair.

The state of the art includes, first of all, the U.S. Pat. No. 4,215 064. This relates to a phosphobetaine of the formula

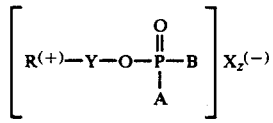

in which
A represents the O—, OM or —O—Y—R(+) group and
B represents the O— or OM group,
X(−) is an anion and
z is a whole number from 0 to 2, with the proviso that only one A or B group can represent O— and that z has a value that is required to balance the charges,
M is a hydrogen group, an organic group or an alkali, alkaline earth or mono-, di- or triethanolamine cation,
R is an amidamine group.

An example of such a phosphobetaine is

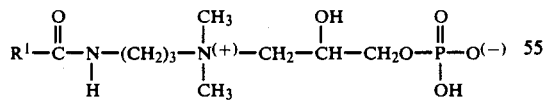

in which $R^1$ is an alkyl group with 7 to 17 carbon atoms.

In the U.S. Pat. No. 4,283,542, the synthesis of these compounds is described in greater detail. According to the claimed method, a phosphate ester of the formula

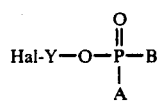

in which Hal is a halogen group and the remaining groups have the above meaning given, is reacted with an amine of the general formula

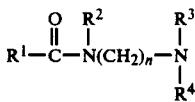

in which
$R^1$ is an alkyl, alkenyl, alkoxy, hydroxyalkyl, aryl or alkaryl group,
$R^2$ is a hydrogen, alkyl, hydroxyalkyl, alkenyl, cycloalkyl or polyoxyalkylene group,
$R^3$, $R^4$ are the same or different and represent alkyl, hydroxyalkyl, carboxyalkyl or polyoxyalkylene groups or, together with the nitrogen atom of the tertiary amine group, can form a heterocyclic ring,
n is a whole number from 2 to 12.
If for example

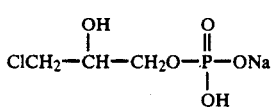

is reacted with 3-cocoamidopropyldimethylamine of the formula

in which $R^1$ represents the average alkyl group of the fatty acids from coconut oil, and contains fatty acids with 7 to 17 carbon atoms, the phosphobetaine of the formula above is obtained.

In the U.S. Pat. No. 4,231,903, detergents and cosmetics are described, which are based on the compounds named above.

A serious disadvantage of these compounds, however, consists therein that, as a consequence of the synthesis process, the compounds contain larger amounts of salt in the form of alkali, alkaline earth or amine salt. Removal of the salt is technically cumbersome, and raises the costs of the products. The high salt content makes the synthesis of anhydrous products appreciably more difficult. This salt content can cause increased corrosion when the phosphobetaines are used in the industrial area. When the products are used in cosmetics, the salt content makes the manufacture of the products more difficult and can lead to skin irritations.

The susceptibility of the aforementioned products to hydrolyze is a further disadvantage. Hydrolysis occurs at the C—O—P bridge

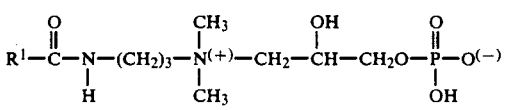

and causes the phosphate group to be split off.

The German Offenlegungsschrift No. 2,260,326 relates to zwitterionic phosphorus compounds of the general formula

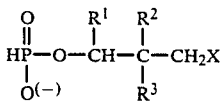

in which
- $R^1$ represents hydrogen or the methyl group,
- $R^2$, $R^3$ represent hydrogen or alkyl groups with 1 to 4 carbon atoms, which may be the same or different,
- X is an ammonium group of the general formula $R^{(+)}$—$R^4R^5R^6$, in which
- $R^4$ represents a hydrogen, alkyl or alkenyl group with 1 to 12 carbon atoms or a —$(C_nH_{2n}O)_zH$ group, in which n=2 or 3 and the sum of all values of z amounts to 1 to 50,
- $R^5$ is a hydrogen, alkyl or alkenyl group with 1 to 20 carbon atoms or a —$(C_nH_{2n}O)_zH$ group and
- $R^6$ is an alkyl or alkenyl group with 1 to 20 carbon atoms or a —$(C_nH_{2n}O)_zH$ group, in which the $R^5$ and $R^6$ groups together with the nitrogen may also form a piperidine, morpholine, imidazole or imidazolin ring.

The compounds may also be synthesized by reacting a cyclic phosphite of the general formula

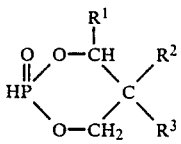

in which $R^1$, $R^2$ and $R^3$ have the meaning already given, at an elevated temperature with a primary, secondary or tertiary amine of the formula $NR^4R^5R^6$ in which $R^4$, $R^5$ and $R^6$ have the above meaning given. The reaction is preferably carried out at temperature of 60° to 150° C in the presence of a polar solvent.

An example of a claimed compound is

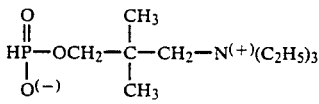

The method of the aforementioned German Offenlegungsschrift No. 2,260,326 enables salt-free phosphobetaines to be synthesized. However, these compounds also contain the —C—O—P bridging element, which is susceptible to hydrolysis.

OBJECT OF THE INVENTION

The object of the invention is to provide phosphobetaines which, while retaining the good surface active properties, are resistant to hydrolysis and during the synthesis of which no alkali, alkaline earth or amine salt is obtained. The novel phosphobetaines shall have affinity for polar surfaces, such as metal or glass surfaces, and for textile fibers or products manufactured from such fibers.

SUMMARY OF THE INVENTION

Pursuant to the invention, this objective is accomplished by the synthesis of novel phosphobetaines of the general formula

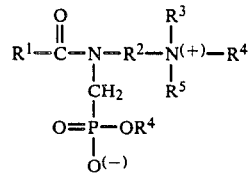

in which
- $R^1$ is an alkyl group with 1 to 20 carbon atoms, optionally substituted with OH groups, or the

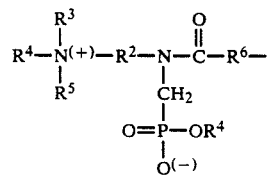

group, in which
- $R^6$ is a divalent alkylene group with 1 to 10 carbon atoms, optionally substituted with OH group,
- $R^2$ is a divalent hydrocarbon group with 2 to 10 carbon atoms, the chain of which may be interrupted by one or more nitrogen atoms,
- $R^3$, $R^5$ are the same or different and represent alkyl or benzyl groups, and
- $R^4$ is an alkyl group with 1 to 4 carbon atoms.

As $R^1$ groups, alkyl groups are preferred, which are derived from a naturally occurring fatty acid or a fatty acid mixture with, on the average, 10 to 20 carbon atoms. Examples of such fatty alkyl groups are lauryl, palmityl, stearyl and oleyl groups. $R^1$ may also represent an OH-substituted alkyl group with 1 to 20 carbon atoms. Examples of such groups are the

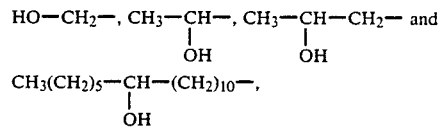

groups, which are derived from glycolic, lactic, 3-hydroxybutyric and 12-hydroxystearic acid.

If the inventive, novel phosphobetaines are derived from aliphatic dicarboxylic acids, those dicarboxylic acids with 2 to 6 carbon atoms in the $R^6$ alkylene group are preferred.

The $R^1$ and $R^6$ groups may be linear or branched; however, linear groups are preferred.

$R^2$ is a divalent hydrocarbon group with 2 to 10 carbon atoms and preferably a divalent aliphatic hydrocarbon group such as the

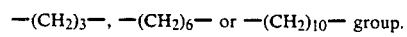

The chain of the divalent hydrocarbon group can be interrupted by one or several nitrogen atoms. This is the case, for example, in the following groups:

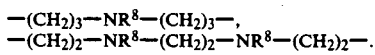

$R^8$ preferably is a lower alkyl group with 1 to 4 carbon atoms.

$R^3$ and $R^5$ may be the same or different. They represent alkyl groups with up to 20 carbon atoms or benzyl groups, alkyl groups, especially lower alkyl groups with 1 to 4 carbon atoms being preferred.

R is an alkyl group with 1 to 4 carbon atoms, the methyl and ethyl groups being preferred.

Examples of inventive phosphobetaines are:

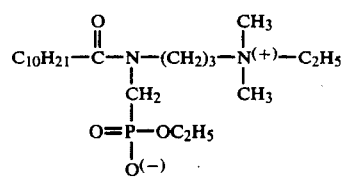

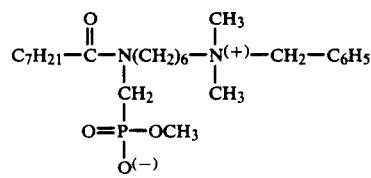

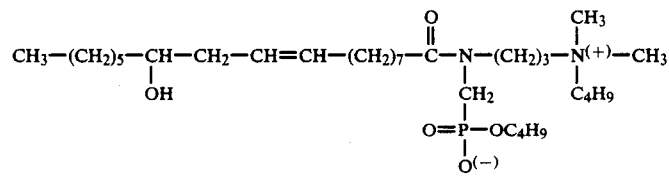

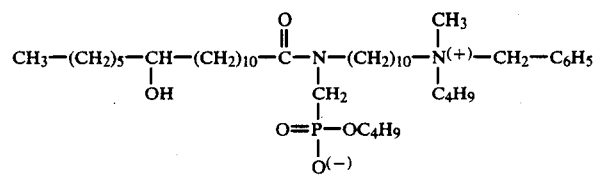

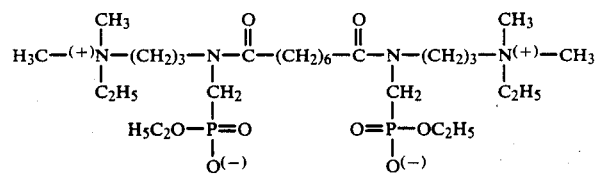

A further aspect of the invention comprises a method for synthesizing the inventive phosphobetaines, which can be carried out simply and in high yield and in which no inorganic salts or amine salts are formed as by-products.

The inventive method is characterized in that compounds of the general formula

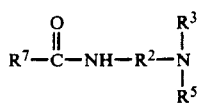
II in which $R^2$, $R^3$ and $R^5$ have the meaning already given and $R^7$ is an alkyl group, optionally with hydroxyl group substituents or the

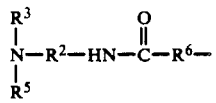

group, in which $R^6$ has the meaning already given, and, based on the tertiary amine groups, at least equimolar amounts of a compound of the general formula

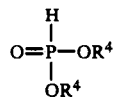
III are dissolved in a polar solvent and a 1.5- to 2-fold molar amount of formaldehyde, based on the amine groups, is slowly added to the solution, the reaction mixture is allowed to react at temperatures of about 60° to 140° C., the water formed is removed by a known procedure and, at the end of the reaction, excess amounts of phosphite ester and formaldehyde, as well as, optionally, the solvent are removed by distillation, preferably under reduced pressure.

As polar solvents, lower aliphatic alcohols, especially ethanol or isopropanol, or ethers, such as tetrahydrofuran or dioxane or a mixture of these solvents can be used.

In Formulas II and III, the $R^2$, $R^3$, $R^4$, $R^5$ and $R^6$ groups have the meaning already given. The $R^7$ groups is defined similarly to the $R^1$ group.

The reaction of the amidamine of Formula II with the ester of the phosphorous acid of Formula III and formaldehyde proceeds in one step and, in a surprising manner, leads directly to the desired betaine. The reaction can be compared to a Mannich reaction. However, it has not yet been described in this form. Especially the spontaneous quaternization of the tertiary nitrogen atom with formation of the betaine structure is surprising to those skilled in the art.

Per mole of tertiary amine group in the amidamine of Formula II, at least one mole of phosphite ester of Formula III is used. Preferably, a slight excess, such as about 1.1 to 1.2 moles of the phosphite ester is used.

The formaldehyde is added to the reaction mixture in amounts of about 1.5 to 2 moles, based on the tertiary amine groups in the amidamine of Formula III. It has proven to be very advantageous to add the amidamine and the phosphite ester to the polar solvent and to dissolve both compounds in the solvent. The formaldehyde, usually as a solution in ethanol or butanol, is then added to this reaction mixture. The reaction commences already at low temperatures and takes place under reflux conditions in about two to five hours.

The reaction temperature lies within the range of about 60° to 140° C. Preferably, the reaction is carried out at a temperature of about 100° to 120° C., especially under reflux conditions.

At the end of the reaction, any excess of reactants is removed from the phosphobetaine. This can be accomplished especially by distillation.

A further aspect of the invention is the use of the inventive, novel phosphobetaines as surface active substances, preferably for the treatment of polar surfaces in the industrial area.

For example, the inventive phosphobetaines are used to great advantage for the cleaning and defatting of metal parts, as emulsifiers for the preparation of cutting and drilling emulsions and as hydrolysis-resistant wetting agents in electroplating. The phosphobetaines protect metal surfaces at least temporarily against oxidation.

Because of their good adhesion to polar surfaces, the phosphobetaines can be used in the finishing of textile fibers or textile fiber products. They provide the textile products with good antistatic properties.

The inventive phosphobetaines are also suitable for the treatment of glass materials. They can be used in the so-called cold-end finishing of glass containers, especially reusable bottles, to reduce wear and for finishing glass fibers.

A further possibility of using phosphobetaines consists in their suitability as dispersants, for example, for dispersing pigments in dyes and paints.

The compounds are excellent wetting agents. Because of their betaine structure, then can be combined with anionic or cationic surfactants or nonionic surfactants. The compounds are resistant to hydrolysis, so that no precipitates are observed during storage in the form of aqueous preparations.

By carefully removing the formaldehyde remaining after the reaction, the inventive, novel phosphobetaines can also be used with outstanding success in cosmetics. The products can be used as shampoos and cosmetics. They have a certain substantivity on hair, without building up on the hair and gluing this together after repeated application. The treated hair is soft and can readily be combed.

In skin care preparations, phosphobetaines can be used especially as mild detergents and cosmetics.

The objects of the present invention are explained in greater detail by means of the following examples, it being understood that these examples are given by way of illustration and not by way of limitation.

EXAMPLE 1

Reactants:

Amidamine: 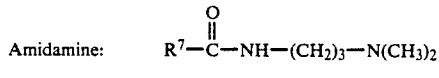

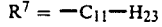

Phosphite Ester: 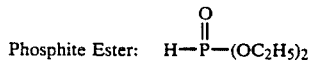

Paraformaldehyde

The amidamine (142.5 g = 0.5 moles) is transferred to a 500 mL flask with reflux condenser. At room temperature, 1 mole = 30.03 g of paraformaldehyde are added. The mixture is heated to 75° C. and stirred for 1 hour at this temperature. Within 20 minutes, 0.55 moles = 75.96 g of diethyl phosphite and 250 mL of xylene are added dropwise. The reaction temperature is raised to 120° C. and the water of reaction is distilled off azeotropically under a slight vacuum. The reaction is allowed to continue for 2 hours at 120° C. The unreacted reactants and the xylene are distilled off by applying a vacuum of 50 mbar. A viscous liquid, which is slightly colored yellow, remains behind. The yield is 98.7% of the theoretical yield.

EXAMPLE 2

Reactants: 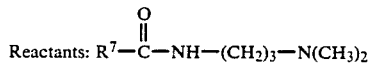

Amidamine: $R^7$ = the alkyl group derived from castor oil fatty acid

Phosphite ester: 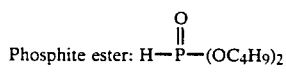

Paraformaldehyde: 30% by weight solution in butanol

The amidamine (1 mole = 382.6 g) is dissolved in 400 mL of butanol and transferred to a 1 L flask with reflux condenser. A formaldehyde solution (2 moles) is added dropwise over a period of 40 minutes. The reaction mixture is heated to 75° C. and stirred for 1 hour. Anhydrous sodium sulfate (100 g) is now added and 1 mole = 194.2 g of dibutyl phosphite is introduced dropwise. Subsequently, the temperature is raised to 85° C. The reaction is allowed to continue for 2.5 hours. The sodium sulfate is filtered off and the reaction mixture is stirred for 3 hours at 125° C. The solvent is then distilled off under atmospheric pressure. A highly viscous golden yellow liquid remains behind. The yield is 94.8% of the theoretical.

EXAMPLE 3

Reactants:

-continued

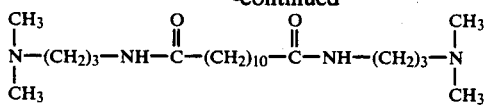

Amidamine:

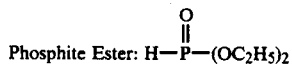

Phosphite Ester: $H-\overset{O}{\underset{\|}{P}}-(OC_2H_5)_2$

Paraformaldehyde: 35% by weight solution in ethanol

The amidamine (0.25 moles=99.66 g) and 0.5 moles=69.05 g of the phosphite ester are dissolved in 150 g of ethanol and transferred to a 500 mL flask with reflux condenser. The temperature of the flask contents is raised to 70° C. and 1 mole=100.09 g of a 30% by weight solution of formaldehyde in ethanol is added dropwise. The reaction mixture is heated to the refluxing temperature and left at this temperature for 5 hours. Excess formaldehyde and ethanol are removed by distillation and passing in argon. A slightly yellow highly viscous product is obtained in a yield of 89.2% of the theoretical.

EXAMPLE 4

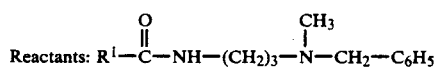

Amidamine: $R^1$ = the alkyl group derived from castor oil fatty acid

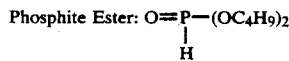

Paraformaldehyde: 30% by weight solution in butanol

The method of Example 2 is repeated, the following amounts being used for the reaction formulation:
- 1 mole=453.7 g of amidamine
- 1 mole=194.2 g of dibutyl phosphite
- 2 mole=200.2 g of a 30% by weight solution of formaldehyde in butanol The yield is 92.4% of the theoretical.

Application Properties of the Inventive Compounds

The compound, obtained in Example 1, is dissolved in distilled water to form a 0.5% by weight solution. The surface tension is determined by the de Nuoy method (ring method). The average value of 10 measurements is 28.8 mN/m.

The corrosion protection test is carried out according to the method of DIN 51360. A value of step 1 to 2 is obtained, whereas the usual, phosphorus-free, commercially available betaines have a value of step 4 to 5. The inventive compounds thus cause no corrosion and can therefore be used as wetting agents in metal processing.

Mixtures of inventive betaines with monoglycerides and diglycerides of stearic acid in a weight ratio of 3:7 to 7:3 show very good emulsifying properties. If such a mixture is added in an amount of about 10 to 20% by weight to solvent naphtha, the latter becomes self emulsifiable. The emulsion obtained is very stable. In the DIN 51360 corrosion test, the emulsions behave like the inventive compounds themselves and cause practically no corrosion.

We claim:

1. A phosphobetaine of the general formula

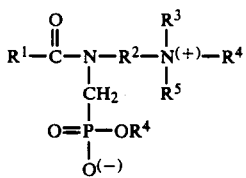

wherein $R^1$ is an alkyl group derived from a natural fatty acid or a mixture of natural fatty acids with, on the average, 10 to 20 carbon atoms, or the group

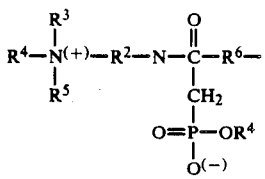

in which $R^6$ is a divalent alkylene group with 1 to 10 carbon atoms, $R^2$ is $-(CH_2)_3-$, $R^3$ is methyl, $R^5$ is methyl or benzyl, and $R^4$ is alkyl with 1 to 4 carbon atoms.

2. A method for the synthesis of a phosphobetaine of the general formula

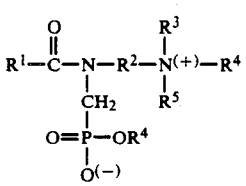

wherein $R^1$ is an alkyl group derived from a natural fatty acid or a mixture of natural fatty acids with, on the average, 10 to 20 carbon atoms, or the group

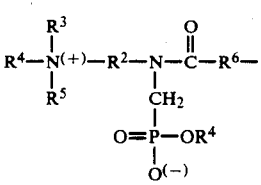

in which $R^6$ is a divalent alkylene group with 1 to 10 carbon atoms, $R^2$ is $-(CH_2)_3-$, $R^3$ is methyl, $R^5$ is methyl or benzyl, and $R^4$ is alkyl with 1 to 4 carbon atoms, which comprises
(a) dissolving or dispersing in a polar solvent a compound of the general formula

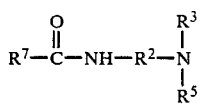

in which $R^2$, $R^3$ and $R^5$ have the above meaning and $R^7$ is an alkyl group, an alkyl group substituted with hydroxyl or the group

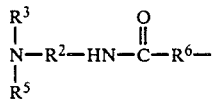

in which $R^2$, $R^3$, $R^5$ and $R^6$ have the above meaning and, based on the available tertiary amine groups, at least equimolar amounts of a compound of the general formula

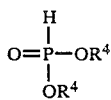

in which $R^4$ has the above meaning,
(b) slowly adding to the solution or dispersion thus obtained a 1.5- or 2-fold molar amount of formaldehyde, based on the available amino groups,
(c) permitting the reaction mixture thus obtained to react at a temperature of about between 60° to 140° C.,
(d) removing water formed during the reaction, and
(e) at the end of the reaction, removing excess amounts of phosphite ester and formaldehyde, as well as any solvent, 3. The method of claim 2, wherein the removal of step (e) is effected by distillation under reduced pressure.

* * * * *